(12) United States Patent
Kamachi et al.

(10) Patent No.: US 7,943,351 B2
(45) Date of Patent: May 17, 2011

(54) METHOD FOR ACYLTRANSFERASE REACTION USING ACYL COENZYME A

(75) Inventors: Motoaki Kamachi, Chiba (JP); Harumi Kamachi, Chiba (JP); Hirobumi Aoki, Chiba (JP); Tomoki Erata, Hokkaido (JP); Kenji Tajima, Hokkaido (JP)

(73) Assignee: Showa Denko K.K., Tokyo (JP)

( * ) Notice: Subject to any disclaimer, the term of this patent is extended or adjusted under 35 U.S.C. 154(b) by 400 days.

(21) Appl. No.: 12/277,622

(22) Filed: Nov. 25, 2008

(65) Prior Publication Data
US 2009/0111153 A1 Apr. 30, 2009

Related U.S. Application Data

(62) Division of application No. 10/542,733, filed as application No. PCT/JP2004/000500 on Jan. 21, 2004, now Pat. No. 7,476,521.

(30) Foreign Application Priority Data

Jan. 22, 2003 (JP) ................................. 2003-013762
Mar. 31, 2003 (JP) ................................. 2003-094881

(51) Int. Cl.
C12P 11/00 (2006.01)
C12P 7/64 (2006.01)
C12P 7/62 (2006.01)
(52) U.S. Cl. .................... 435/130; 435/134; 435/135
(58) Field of Classification Search .................. None
See application file for complete search history.

(56) References Cited

U.S. PATENT DOCUMENTS 4,393,167 A 7/1983 Holmes et al.
6,495,152 B2 * 12/2002 Steinbuchel et al. ......... 424/405

FOREIGN PATENT DOCUMENTS

| EP | 0114086 A2 | 7/1984 |
| EP | 0274151 A2 | 7/1988 |
| JP | 63-269989 A | 11/1988 |
| JP | 64-048821 A | 2/1989 |
| JP | 01-156320 A | 6/1989 |
| JP | 01-222788 A | 9/1989 |
| JP | 05/093049 A | 4/1993 |
| JP | 07-265065 A | 10/1995 |
| JP | 10-108682 A | 4/1998 |
| WO | 99/14313 A2 | 3/1999 |
| WO | 02/08428 A2 | 1/2002 |

OTHER PUBLICATIONS

Ouyang et al, "A new chemical method for synthesizing and recycling acyl coenzyme A thioesters", J. of Organic Chemistry, 56(11):3752-3755 (1991).

Nagiec et al, "The LCB2 gene of saccaromoyces and the related LCB1 gene encode subunits of serine palmitoyltransferase, the initial enzyme in sphingolipid synthesis", Proc. Natl., Acad. Sci., USA, 91:7899-7902 (1994).

Antonio et al, "Analysis of in vivo substrate specificity of the PHA synthase from *Ralstonia eutropha*: formation of novel copolyesters in recombinant *Escherichia coli*", FEMS Microbiology Letters, 182(1):111-117 (2000).

Yuan et al, "Class I and III polyhydroxyal Kanoate synthases from *Ralstonia eutrpha* and *Allochromatium vinosum*; characterization and substrate specificity studies", Archives of Biochemistry and Biphysics, 394(1):87-98 (2001).

Narimatsu et al, "Solubilization and partial characterization of fatty acyl-CoA: sphingosine acyltransferase (ceramide synthetase) from rat liver and brain", Biochimica et Biophysica. Acta., 877(3):334-341 (1986).

Theodor Wieland et al., "Synthese von S-β-Oxybutyryl- und S-Acetacetyl-Coenzym A", Angew. Chem., 1953, 7: pp. 186-187.

Kumar D. Mukherjee et al., CRC Handbook of Chromatography: Analysis of Lipids, 1993, CRC Press, Inc., Chapter 21, pp. 285-320.

* cited by examiner

*Primary Examiner* — Herbert J. Lilling
(74) *Attorney, Agent, or Firm* — Sughrue Mion, PLLC

(57) ABSTRACT

The present invention relates to a method for acyltransferase reaction in which an acyl group of acyl coenzyme A is transferred to an acyl group receptor characterized in that the reaction is carried out by production and/or reproduction of acyl coenzyme A from coenzyme A in a reaction system by a chemical thioester exchange reaction with acylthioester. The present invention, wherein expensive acyl CoA is reproduced nonenzymatically in a reaction system, enables to continuously carry out acyltransferase reaction only by putting a small amount of acyl CoA with a donor and a receptor of an acyl group into a system. Accordingly, the method of the present invention can be applied to an industrial production method of various kinds of compounds including useful biological molecules and synthesis of polymers such as polyester.

13 Claims, 1 Drawing Sheet

METHOD FOR ACYLTRANSFERASE REACTION USING ACYL COENZYME A

CROSS-REFERENCE TO RELATED APPLICATIONS

This application is a Divisional of U.S. application Ser. No. 10/542,733, filed Jul. 20, 2005 now U.S. Pat. No. 7,476,521; which is a 371 of PCT/JP2004/000500 filed Jan. 21, 2004; the disclosures of each of which are incorporated herein by reference in their entirety.

TECHNICAL FIELD

The present invention relates to a method for acyltransferase reaction for transferring an acyl group to various organic compounds by acyl coenzyme A (hereinafter, coenzyme A may be referred to as CoA). More particularly, it relates to a novel method for acyltransferase reaction in which the reaction is continuously carried out without additional use of a very expensive acyl CoA in a production process of an acyl compound using acyltransferase to significantly improve its productivity whereby to enable acyltransferase to be utilized for industrial production process of various compounds.

The present invention further relates to a CoA enzyme coupling method where a chemical thioester exchange reaction is used as an acyl CoA reproduction system.

The present invention furthermore relates to a production process of important physiologically active substances such as a sphingolipid using CoA enzyme.

The present invention still further relates to a production process of macromolecular compounds by an enzymatic reaction. More particularly, it relates to an efficient production process of biodegradable macromolecular compounds, particularly polyester, where acyl coenzyme A (acyl CoA) is reproduced in a reaction system in the co-presence of a thioester exchange reaction and an enzymatic polymerization reaction whereby macromolecular compounds are able to be continuously synthesized from thioesters.

BACKGROUND ART

CoA is a substance which functions as an acyl carrier/acyl activator in all biological species. For example, in addition to the fact that acetyl CoA is a key substance for important biological metabolism of fatty acid, glucose, etc. via a citric acid cycle, some kinds of acyl CoA derivatives play an important role in biosynthesis of cholesterol and fatty acid as well. CoA is essential as an auxiliary factor (coenzyme) for an enzymatically catalyzing reaction (CoA enzyme) concerning such a metabolism, is a substance which is unable to be substituted with others and is represented by the following formula.

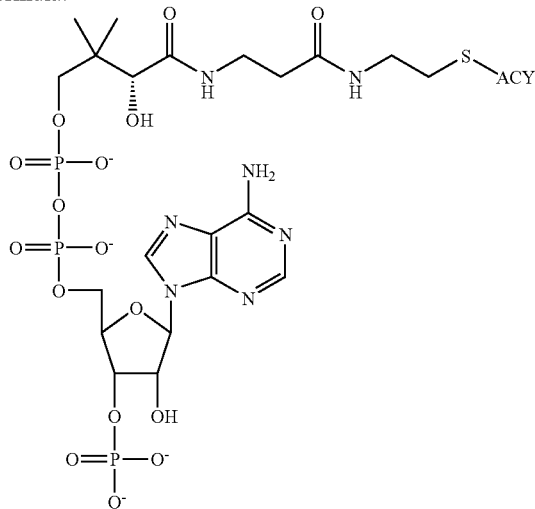

(In the Formula, ACY is an Acyl Group.)

In CoA enzyme, there are various CoA enzymes depending upon the structure and the substrate (a compound into which an acyl group is to be introduced) of an acyl group to be transferred. Up to now, many attempts have been made for the production of a substance using various kinds of CoA enzymes and, for example, there are examples for the production of antibiotics and drugs, various chemical substances utilizing a polyketide synthesis route, amino acids, polyhydroxy acids, etc.

In those methods, equimolar acyl CoA is consumed as an acyl group receptor. Accordingly, it is required that the necessary acyl CoA is produced at a low cost.

In any of the above-mentioned methods, acyl CoA in vivo which is fermentationally produced by fermentation or acyl CoA which is produced separately from the production system is used. When acyl CoA in vivo fermentationally produced is used, only a specific acyl CoA produced in vivo such as acetyl CoA or malonyl CoA is able to be utilized. In order to solve such a problem, there has been reported an art where an enzymatic ester exchange is carried out between acetyl CoA and various fatty acids to produce acyl CoA in vitro. The method where acyl CoA which is separately produced from the production system is used has a multiplicity of uses and is a method which has been commonly used but the acyl CoA which is produced as such is very expensive and it is still necessary to use equimolar amount when used for a transfer reaction of an acyl group.

With regard to a production process of acyl CoA, a chemical synthetic method using an acyl chloride, a chemical synthetic method using an acid anhydride, a chemical synthetic method using a mixed acid anhydride with ethyl chlorocarbonate, a chemical synthetic method by a thioester exchange (Z. Naturforsch. 29C, 469-474 (1974); Z. Naturforsch. 30C, 352-358 (1975); J. Am. Chem. Soc., 1953, 75, 2520; J. Biol. Chem., 1985, 260, 13181) and many other chemical synthetic methods have been generally used. However, in many of the chemical synthetic methods, selectivity to thiol group is low in general and there is a problem that the yield is lowered by a non-selective acylation reaction. Although these production processes have been used even today, they are merely used for a laboratory production of acyl CoA.

In order to overcome the weak points of the chemical synthetic method, an enzymatic production process of acyl CoA has been also studied vigorously. Thus, a method using an acetyl CoA synthetic enzyme, a method using a fatty acid CoA synthetic enzyme, etc. have been reported (Appl. Microbiol. Biotechnol., 1994, 40, 699-709). However, in those enzymatic reaction methods, it is very difficult to obtain the enzyme which serves as a catalyst in a necessary amount.

With regard to a production process using an enzyme, a study concerning a coupling method in cooperation with a CoA enzyme reaction using it as an acyl CoA reproduction system has been reported. That is, the acyl CoA consumed by an acyl group transfer reaction is reproduced by an enzymatic reaction and used for the reaction again and there are a coupling method using phosphotransacetylase, a coupling method using carnitine acetyltransferase, a coupling method using an acetyl CoA synthetic enzyme, a coupling method using an α-ketoglutaric acid dehydrogenase, etc. These methods have a high selectivity to thiol group and particularly an acetyl CoA synthetic enzyme has wide substrate selectivity and is useful because various kinds of acyl CoAs are able to be generated.

However, these methods reproduce an acyl CoA by enzyme and each of them has problems including that such an enzymatic reproduction system has a slow reaction rate, enzyme is unstable, ATP and a relatively expensive auxiliary component are necessary for the reaction and no reaction is possible in CoA of high concentrations. Thus, unless the price of the aimed product is considerably high, they are generally said to be unable to be industrial production methods in terms of cost if an acyl CoA is used for less than 10,000 times. Consequently, the above-mentioned methods are not satisfactory as industrial production methods. Although there is an attempt to reproduce an acetyl CoA utilizing a non-enzymatic reaction using an N-acetyl substance of dimethylaminopyridine (*Bioorganic Chem.*, 1990, 18, 131-135), it is a bilayer system using a large quantity of an organic solvent whereby there is a problem in view of purification of the product and the method is not suitable for an industrial production.

As mentioned above, an acyl CoA reproduction system which is satisfactory for enabling the utilization of a CoA enzyme as an industrial production method has not been known up to now.

Sphingolipid is a lipid derived from a sphingoid base such as sphingosine and is present in cell membranes of animals, plants and microbes. Although a precise function of human sphingolipid has not been known yet, a group of such compounds participates in electric signal transmittance in a nervous system and stabilization of cell membranes. Sphingoglycolipid has a function in immune system and it has been shown that a specific sphingoglycolipid functions as a receptor for bacterial toxin and also probably as a receptor for microbes and viruses.

Ceramide is a specific group of sphingolipid containing sphingosine, dihydrosphingosine or phytosphingosine as a base. Ceramide is a main lipid component of horny layer which is an upper layer of the skin and has an important barrier function. It has been known that a topical application of a composition containing a sphingolipid such as ceramide improves, for example, a barrier function and a moisture-retaining characteristic of the skin (Curatolo, *Pharm. Res.*, 4: 271-277 (1987); Kerscher, et al., *Eur. J. Dermatol.*, 1:39-43 (1991)).

It has been known that a sphingoid base per se inhibits the activity of protein kinase C which is an important enzyme in a signaling pathway and accordingly that it mediates several physiological actions. Moreover, a sphingoid base is contained in cosmetic compositions or in dermatological compositions due to its anti-inflammatory activity and antibacterial activity.

At present, heterosphingolipid preparations for cosmetics are mostly extracted from animal sources. However, that is a method which is relatively expensive in an industrial scale and a public concern is increasing for novel material sources for pure and structurally specified sphingolipid which is available from other supplying sources than animal tissues because of, for example, a latency of bovine spongiform encephalopathy (BSE).

It has been found that microbe such as *Pichia ciferrii* yeast produces sphingolipid, sphingosine, phytosphingosine and/ or derivatives thereof (Wickerham and Stodola, *J. Bacteriol.*, 80:484-491 (1960)). Such a microbe provides supplying source for sphingolipid per se and supplying source for starting material for production of other commercially valuable compounds and gives an practically applicable substitute to the use of animal supplying source for those compounds. However, in the production by microbes, improvement in productivity is difficult because of toxicity of a sphingoid base to microbe cells (Pinto, et al., *J. Bacteriol.*, 174:2565-2574 (1992); Bibel, et al., *J. Invest. Dermatol.*, 93:269-273 (1992)) and there has been a brisk demand for providing more efficient production process.

In addition, as a result of increasing consciousness to environmental issues in recent years, there is much more interest in biodegradable macromolecules being friendly to environment than in synthetic macromolecules which have occupied the main stream.

Polyhydroxy alkanoate (hereinafter, may be abbreviated as PHA) which is one of biodegradable macromolecules is a polyester being usually produced by a fermentation production of microbes and receiving public attention due to its high biodegradability and 90 or more kinds have been known (*FEMS Microbiol. Lett.*, 1995, 128, 219-228). Among them, research and development have been promoted for poly(3-hydroxybutyrate) (hereinafter, may be abbreviated as PHB), poly(3-hydroxyvalerate) (hereinafter, may be abbreviated as PHV) and poly(3-hydroxybutyrate-co-3-hydroxyvalerate) (hereinafter, may be abbreviated as PHB-co-PHV) due to ease of produce and good characteristics (Japanese Laid-Open Patent Publication No. 57-150393 (U.S. Pat. No. 4,393, 167), Japanese Laid-Open Patent Publication No. 59-220192 (European Patent Laid-Open No. 0114086), Japanese Laid-Open Patent Publication No. 63-226291 (European Patent Laid-Open No. 0274151) and Japanese Laid-Open Patent Publication No. 63-269989). However, there are many problems in PHA that, the productivity is low in the production by fermentation of microbe in order to accumulate PHA in microbe cells and that, in addition, it takes much cost for purification by crushing microbes and extracting PHA.

Since then, analysis of the mechanism of fermentation production has proceeded, which increased accumulated concentration of PHA into the microbe cells significantly, and also analysis of mechanism of accumulated state of PHA into microbe cells has proceeded, which lowered cost for extraction and purification of PHA from microbes whereby actual production of PHA using microbes has started.

In addition, since it has been in the meanwhile clarified that there are varieties of microbes which produce PHA, research and development of PHA other than PHB, PHV and PHB-co-PHV has made substantial progress and research and development of copolymers for improving the physical property have been also carried out (Japanese Laid-Open Patent Publication Nos. 63-269989, 64-048821, 01-156320, 01-222788 and 05-093049).

However, since a production process of PHA by fermentation production of microbe proceeds via a complicated biometabolic path, the desired PHA is not always produced and, moreover, variation of PHA is limited as well. Further, depending upon a method for controlling the fermentation production, a desired homopolymer is not produced but a copolymer is formed and, reversely, a homogeneous copolymer in a desired polymerization ratio is not always produced in a production of copolymer (*FEMS Microbiol. Rev.*, 1992, 103, 207-214). In addition, in a purification step, since a desired PHA is taken out from microbe cells containing many kinds of compounds, there is a limitation in improving purity in an industrial production. As such, production of PHA by fermentation of microbes has various problems.

On the other hand, by a genetic recombination technique which has quickly progressed in recent years, gene of polyhydroxyalkanoate synthase (PHAS) which is an enzyme copolymerizing PHA was isolated and, by enhancing its expression, improvement of production of PHA has been also attempted (Japanese Laid-Open Patent Publication Nos. 07-265065, 10-108682 and 2001-516574 (WO 99/14313)).

Further, it is now also possible to separate and purify PHAS in large quantities using a genetic recombination technique and a method for polymerization of PHB in vitro without using a microbe fermentation has been developed whereby homogeneous and highly pure PHB is able to be produced (*Proc. Natl. Acad. Sci.*, 1995, 92, 6279-6283,; *Int. Symp. Bacterial Polyhydroxyalkanoates*, 1996, 28-35; *Eur. J. Biochem.*, 1994, 226, 71-80; *Appl. Microbiol. Biotechnol.*, 1998, 49, 258-266; *Macromolecules*, 2000, 33, 229-231).

After that, it has been shown that PHA other than PHB is also able to be synthesized by the similar in vitro polymerization method and there is no limitation on variation of PHA which has been unable to be achieved by a microbe fermentation method whereby it is suggested that variation of PHA is significantly expanded (*Biomacromolecules*, 2000, 1, 433-439; *Appl. Microbiol. Biotechnol.*, 2001, 56, 131-136; *Macromolecules*, 2001, 34, 6889-6894). In that method, it is also possible to synthesize copolymers in addition to homopolymers.

However, acyl CoA is to be used as a starting substance for the polymerization in an in vitro polymerization method, but, as mentioned above, there are various problems for the synthesis of acyl CoA.

Accordingly, there has been a demand for suppressing the amount of an acyl CoA used very small and also for developing a production process of macromolecular compounds where other compound which is easily synthesized industrially is used as a starting substance.

On the other hand, in an in vitro polymerization method, acyl CoA is used as a substrate for enzyme and the enzyme reacts whereupon PHA is polymerized and, at the same time, liberated CoA is discharged into the reaction system (refer to the following formula).

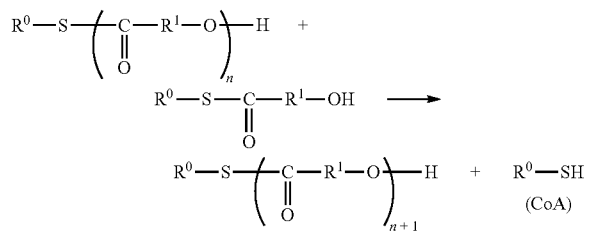

(In the formula, $R^0$ is an organic group wherein $R^0$—SH is CoA; $R^1$ is any alkylene; and n is an integer corresponding to degree of polymerization.)

As such, each time when a reaction of acyl group transfer from acyl CoA takes place, one repeating unit is added whereupon one molecule of CoA is released.

In an in vitro polymerization method, this CoA remains in a reaction system in its free state just to be accumulated therein and the yield of a macromolecular polymerization reaction does not exceed the equivalent amount of the acyl CoA which is put into the reaction system. Therefore, productivity of PHA is very low and cost of PHA manufactured by an in vitro polymerization method is nothing but quite expensive. As the polymerization proceeds further, CoA concentration in the reaction system increases whereby there are concerns about an inhibition effect to the enzymatic reaction as well.

Incidentally, as an effective utilization method of CoA which is present in a high concentration in the reaction system in a free state, its reproduction is attempted as well (*FEMS Microbiology Letters*, 1998, 168, 319-324). That is, acetic acid, acetyl CoA synthetase and ATP are made coexisted in a polymerization enzymatic reaction solution whereby CoA which is liberated after the polymerization reaction is converted to acetyl CoA and, in addition, propionyl CoA transferase and 3-hydroxybutyrate are also made coexisted to give 3-hydroxybutyrate CoA which is a substrate for the polymerization catalyst. In that method however, as many as three kinds of enzymes which are very difficult to purify are used and, further, quite expensive ATP is also necessary whereby it is very difficult to apply it to an industrial production process.

As such, in an in vitro polymerization method, it is necessary to use an acyl CoA as a reaction substrate and, since acyl CoA is very expensive, it is quite difficult to lower the production cost of PHA when acyl CoA is used as a reaction substrate for an industrial production of PHA. Moreover, in a reproduction of CoA to acyl CoA, many kinds of enzymes which are difficult to obtain are necessary and, in addition, an expensive compound such as ATP is necessary. Further, in a production process of PHA using living organism or, particularly, microbe, variation of PHA is limited and, furthermore, there is a high possibility that copolymer is polymerized due to metabolism in living body whereby it is difficult to produce a desired PHA only. In view of the above, there has been a demand for developing a production process which enables greater variation of PHA, and can lower the production cost of PHA by using a compound which is easily able to be synthesized in its production as a starting substance.

DISCLOSURE OF THE INVENTION

An object of the present invention is to provide an industrial acyltransferase reaction method using a CoA enzyme in an acyl CoA reproduction system and, particularly, to provide an acyltransferase reaction method which is useful for the production of a physiologically active substance such as biological material.

Another object of the present invention is to provide an entirely novel semi-synthetic production process to produce a useful sphingoid base by an enzymatic reaction. Still another object is to provide an economical method where an effective production of sphingoid base is possible using a coenzyme (CoA) of a catalytic amount.

Further object of the present invention is to provide a process for an effective production by a coenzyme (CoA) of a catalytic amount in the production of a biodegradable macromolecular compound useful for an enzymatic reaction.

The present inventors have extensively studied a reproduction system of acyl CoA concerning efficiency, speed, cost and selectivity and also whether a coupling is possible between the reproducing reaction and an enzymatic reaction. As a result, it has been found that a thioester exchange reaction which is a chemical synthetic method so far used only for preparation is able to be coupled with an enzymatic reaction system whereupon the present invention has been achieved.

The thioester exchange reaction proceeds in a system of neutral to weakly basic region and a substrate specificity of acyl group is very broad whereby it can be coupled with any CoA enzyme showing a reactivity within a region in which a thioester exchange reaction can take place.

Further, the present inventors have applied this coupling method to a serine C-palmitoyl transferase which is a key enzyme in a biosynthesis pathway for sphingolipid and succeeded in establishing a production method and the like for the production of a sphingoid base which is an important physiologically active substance by a decarboxylating transfer reaction of fatty acid chain via CoA using a tiophenyl fatty acid and serine.

Still further, in order to develop a production process of PHA in high efficiency, the present inventors have eagerly investigated to find a novel synthetic pathway for various compounds related to PHA from an organic compound. As a result, they have found that, when a thioester exchange reaction is combined with an in vitro polymerization method, a starting substance for the reaction can be substituted with an easily synthesizable thiophenyl ester and a reproduction reaction of an acyl CoA which is essential in the polymerization reaction is also able to be conducted in the same reaction solution system whereby consumed amount of acyl CoA can be dramatically reduced together with suppression of concentration of CoA. Thus, the present invention has now been achieved.

Accordingly, the present invention relates to the following acyltransferase reaction method.

1. A method for acyltransferase reaction in which an acyl group of acyl coenzyme A (acyl CoA) is transferred characterized in that the reaction is carried out by production and/or reproduction of acyl coenzyme A from coenzyme A in a reaction system by a chemical thioester exchange reaction with an acyl group donor which is an acyl ester of a thiol compound.
2. The method for acyltransferase reaction according to 1 above, wherein an acyl group donor, acyl group receptor, coenzyme A and acyltransferase are contained in the reaction system at the same time, an acyl group of the acyl group donor is transferred to coenzyme A by a chemical thioester exchange reaction to give an acyl coenzyme A and an acyl group of the acyl coenzyme A is transferred to the acyl group receptor.
3. The method for acyltransferase reaction according to 2 above, wherein the method is carried out together with production and/or reproduction of acyl coenzyme A by an acyl group of the acyl group donor.
4. The method for acyltransferase reaction according to 2 above, wherein the thiol compound is aromatic thiol.
5. The method for acyltransferase reaction according to 4 above, wherein the aromatic thiol is thiophenol which may optionally contain a substituent group(s).
6. The method for acyltransferase reaction according to 2 above, wherein the acyl group receptor is amino acid and/or a derivative thereof.
7. The method for acyltransferase reaction according to 2 above, wherein the acyl group receptor is serine and/or a derivative thereof.
8. The method for acyltransferase reaction according to 1 or 2 above, wherein the acyltransferase is serine C-palmitoyl transferase.
9. The method for acyltransferase reaction according to 8 above, wherein the serine C-palmitoyl transferase is derived from bacteria of genus *Sphingomonas*.
10. The method for acyltransferase reaction according to 1 or 2 above, wherein the acyltransferase is a sphingosine N-acyl transferase.
11. The method for acyltransferase reaction according to 2 above, wherein the acyltransferase is a macromolecular polymerization enzyme and a macromolecular compound is synthesized in a reaction in which an acyl group donor, acyl group receptor, coenzyme A and acyltransferase are contained in the reaction system at the same time, an acyl group of the acyl group donor is transferred to coenzyme A by a chemical thioester exchange reaction to give an acyl coenzyme A and an acyl group of the acyl coenzyme A is transferred to the acyl group receptor.
12. The method for acyltransferase reaction according to 11 above, wherein an acyltransferase reaction is repeated using acyl coenzyme A or a product by the acyltransferase reaction as an acyl group receptor whereby the macromolecular compound is produced.
13. The method for acyltransferase reaction according to 11 above, wherein the acyl thioester is acyl ester of aromatic thiol.
14. The method for acyltransferase reaction according to 13 above, wherein the acyl ester of aromatic thiol is hydroxyalkanoate thiophenyl ester.
15. The method for acyltransferase reaction according to 14 above, wherein the hydroxyalkanoate thiophenyl ester is 3-hydroxyalkanoate thiophenyl ester.
16. The method for acyltransferase reaction according to 15 above, wherein the 3-hydroxyalkanoate thiophenyl ester is 3-hydroxybutyrate thiophenyl ester.
17. The method for acyltransferase reaction according to 11 above, wherein the macromolecular polymerization enzyme is polyhydroxy alkanoate synthase.
18. The method for acyltransferase reaction according to 17 above, wherein the polyhydroxy alkanoate synthase is derived from genus *Ralstonia*.
19. The method for acyltransferase reaction according to 18 above, wherein the genus *Ralstonia* is *Ralstonia eutropha*.
20. The method for acyltransferase reaction according to 19 above, wherein *Ralstonia eutropha* is *Ralstonia eutropha* ATCC 17699.
21. A production process of a sphingoid base using the acyltransferase reaction described in any of 7 to 9 above.
22. The product on process according to 21 above, wherein the sphingoid base is 3-ketodihydrosphingosine.
23. A production process of a ceramide using the acyltransferase reaction described in 10 above.
24. In a production process of a macromolecular compound using the acyltransferase reaction described in any of 11 to 20 above, a production process of polyester in which the macromolecular compound is polyester.
25. The production process of the polyester according to 24 above, wherein the polyester is polyhydroxy alkanoate.
26. The production process of the polyester according to 25 above, wherein the polyhydroxy alkanoate is poly(3-hydroxy alkanoate).
27. The production process of the polyester according to 26 above, wherein the poly(3-hydroxy alkanoate) is poly(3-hydroxy butyrate).

DETAILED DESCRIPTION OF THE INVENTION

Figure 1:
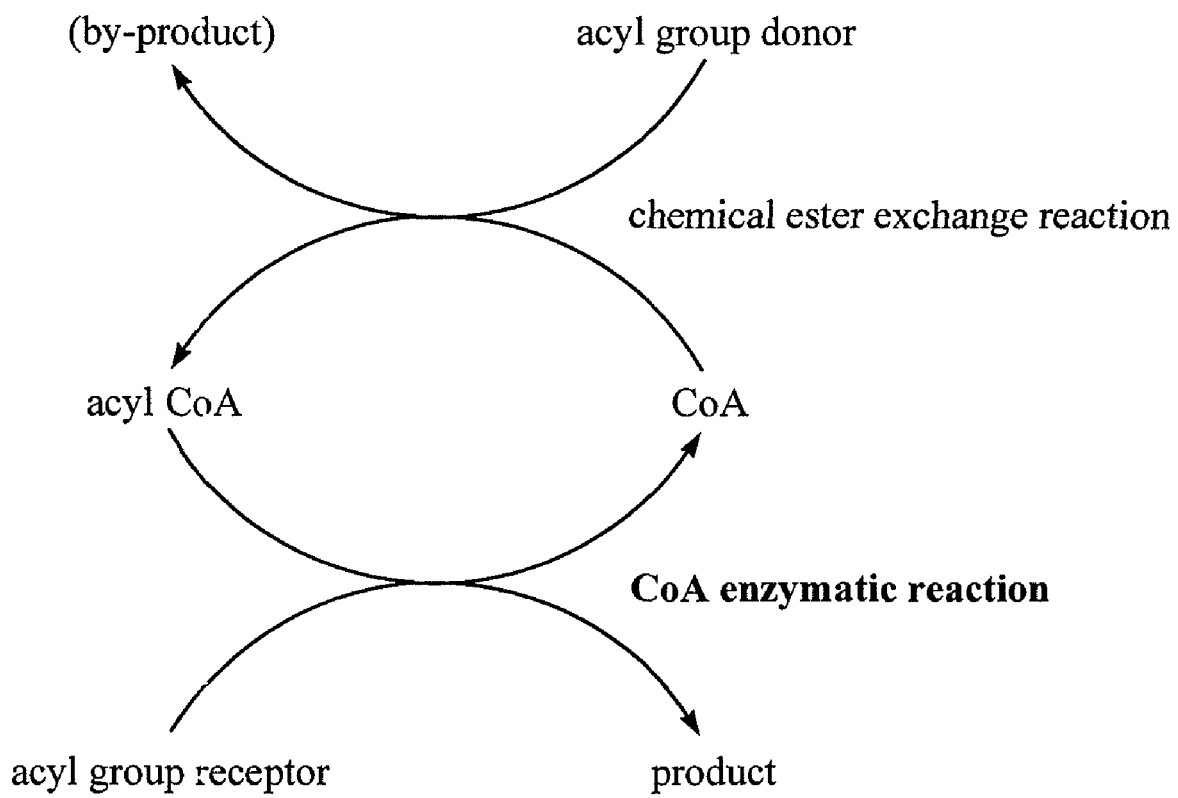
FIG. 1 is a scheme which shows a coupling reaction of a CoA enzyme reaction with an acyl CoA reproduction system by a thioester exchange according to the present invention.

According to the present invention, as shown in FIG. 1, an acyl group donor, acyl group receptor, CoA and acyltransferase (CoA enzyme) exist in one system and an acyl group transfer reaction is able to be carried out by a coupling reaction where acyl CoA consumed by the progress of the reaction is produced and reproduced by a chemical thioester exchange reaction of the acyl group donor with the coenzyme A in the same system as an enzymatic reaction.

In an embodiment of the present invention, acyl CoA consumed by the progress of the reaction is produced and reproduced by a chemical thioester exchange reaction. As a result, an efficient acyl group transfer reaction is able to be achieved only by the presence of a small amount of acyl CoA which is expensive.

In another embodiment of the present invention, acyl CoA or the product by an acyl group transfer reaction is further made into an acyl group receptor. As a result, an efficient polymer producing reaction is able to be achieved by repetition of an acyl group transfer reaction.

The above-mentioned second embodiment (reaction for the production of a polymer) is a part of the above-mentioned first embodiment (a highly efficient acyl group transfer reaction) and, hereinafter, the first embodiment (a highly efficient acyl group transfer reaction) and the second embodiment (a reaction for the production of polymer) will be illustrated separately for the sake of convenience.

(1) Highly Efficient Acyl Group Transfer Reaction
(1-1) CoA Enzyme

With regard to the CoA enzyme used in this embodiment, there is no particular limitation so far as it uses an acyl CoA as an auxiliary factor (coenzyme). Examples of such an enzyme are transferases belonging to a series of "EC 2.3.1.x" such as acetylglutamic acid synthase (EC 2.3.1.1), acetoacetyl CoA thiolase (EC 2.3.1.9) and serine C-palmitoyl transferase (EC 2.3.1.50). It has been made clear already that those enzymes are present in many living organisms and they have been separated from various living organisms and purified already (Enzyme Nomenclature, 178-199, Academic Press, Inc. (1992)). Among those, enzymes having optimum pH in neutral to weakly basic regions are preferred. Although those CoA enzymes may be pure ones, it is also possible to use catalytic microbe cells having an CoA enzymatic activity or a processed product thereof. In that case however, it is desirable that influence of enzymes other than for the purpose of using acyl CoA as an auxiliary factor are to be avoided by means of use of defective mutant, inhibition of activity, inactivating treatment, etc.

(1-2) Acyl Group Donor

With regard to an acyl group donor used in the highly efficient acyl group transfer according to the present invention, there is no limitation so far as it is acyl ester of a thiol compound (in the present application, it may be merely referred to as "acylthioester") by which a thioester exchange reaction with CoA takes place in a non-catalytic manner, but an acyl ester of aromatic thiol is preferred. Examples of the aromatic thiol are thiophenol, methylthiophenol, chlorothiophenol, 2-mercaptothiazole, 2-mercaptoimidazole, 2-mercaptotriazole, 2-mercaptobenzothiazole, 2-mercaptobenzimidazole and 2-mercaptopyridine. Particularly preferred examples are acyl ester of thiophenol (which may be merely referred to as "thiophenyl ester" in the present application including the case where the phenyl group is substituted).

With regard to an acyl group corresponding to the acyl ester thiol, any acyl group may be fundamentally used without limitation. Examples thereof are a $C_2$ to $C_{20}$ saturated or unsaturated aliphatic acyl group such as acetyl ($CH_3CO-$), propionyl ($CH_3CH_2CO-$), butyryl ($CH_3CH_2CH_2CO-$), isobutyryl (($CH_3)_2CHCO-$), acryloyl ($CH_2=CH-CO-$) methacryloyl ($CH_2=C(CH_3)-CO-$), palmitoyl ($CH_3-[CH_2]_{14}-CO-$), stearoyl ($CH_3-[CH_2]_{16}-CO-$) and oleoyl ($CH_3-[CH_2]_6-CH=CH-[CH_2]_6-CO-$) and an aromatic acyl group such as benzoyl. Of course these are mere exemplifications and, for example, an alkyl chain of the aliphatic acyl group may be substituted and a part of or all of them may be cyclic. The aromatic ring of the aromatic acyl group may be a carbocyclic ring, a hetero ring or a fused ring and may be optionally substituted. Examples of the substituent group are a hydroxyl group, an alkyl group, an aryl group, an aralkyl group, an amino group and halogen such as chlorine and bromine.

(1-3) Acyl Group Receptor

With regard to the acyl group receptor used in the highly efficient acyl group transfer reaction according to the present invention, there is no limitation so far as it is able to be used as a substrate for the above CoA enzyme. When a substrate specificity of the enzyme is changed by the reaction condition or when a mutant where the substrate specificity is modified by means of protein engineering is used, a substance which is not usually an appropriate substrate for the enzyme is also able to be used as an acyl group receptor.

Preferred acyl group receptors are amino acid and amino acid derivative and particularly preferred ones are natural amino acid and nonnatural amino acid. For example, when an amino acid is serine and an enzyme is serine C-palmitoyl transferase, an efficient synthetic reaction for 3-ketodihydrosphingosine is resulted. When an acyl group receptor is sphingosine which is an amino acid derivative and an enzyme is sphingosine N-acyl transferase, an efficient synthetic reaction for ceramide is resulted. Incidentally, a product in the acyl group transfer reaction does not always have a transferred acyl group as it is but may be decarboxylated or rearranged under the reaction condition and, generally, it depends upon the enzyme and the substrate used therefor.

(1-4) Reaction Condition

The CoA used in the highly efficient acyl group transfer reaction according to the present invention may be a product manufactured by any of the methods of chemical synthesis, semi-synthesis, biological fermentation, etc. so far as it is able to function as CoA.

With regard to the reaction system used in the highly efficient acyl group transfer reaction according to the present invention, there is no limitation so far as it is a system where an ester exchange reaction between an acyl group donor and CoA and an acyl group transfer reaction from an acyl CoA to an acyl group receptor by the CoA enzyme used proceed at the same time and it is possible to use an aqueous uniform system, an organic solvent uniform system or a bilayer system of an organic solvent and water.

With regard to the reaction of the present invention, it may take place at a temperature where stability of the CoA enzyme is ensured and the reaction proceeds. Usually, the reaction temperature is 10° C. to 45° C. and, preferably, 20° C. to 40° C.

There is no particular limitation on the concentration in the reaction of the present invention so far as stability of the CoA enzyme is ensured and the reaction proceeds.

The reaction system may be an open type or a tightly closed type and, when smell or the like is a problem, the reaction may be carried out in a tightly closed system.

(2) Reaction for Production of Macromolecular Compound
(2-1) Macromolecular Compound As mentioned above, the present invention is also useful as a reaction for the production of a macromolecular compound and, to be more specific, it relates to a production process of a macromolecular compound where a macromolecular compound is synthesized from a thioester in a solution where a thioester exchange reaction and a macromolecular polymerization enzyme reaction are made co-existed.

With regard to the macromolecular compound synthesized in the present invention, there is no limitation so far as it is a macromolecular compound synthesized from a thioester in a solution where a thioester exchange reaction and a macromolecular polymerization enzyme reaction are made co-existed, and an example thereof is a polyhydroxy alkanoate (PHA) which has been reported to be produced mainly by fermentation production of microorganism up to now. It has been known that 90 or more kinds thereof are available (*FEMS*

*Microbiol. Lett.* 1995, 128, 219). More specific examples are a compound having $C_2$ or higher alkyl chain in a side chain, which compound may have $C_6$ or more or $C_{10}$ or more long-chain alkyl group; a compound having a branched alkyl group in the side chain; a compound having a phenyl ring in the side chain, which compound may have a modified group on the phenyl ring; a compound having a phenoxy ring in the side chain, which compound may have a modified group on the phenoxy ring; a compound having a double bond or a triple bond in the side chain, which may exhibit a good polymerizing property; a compound having a halogen element in the side chain; a compound having a cyclo ring in the side chain; and a compound having an epoxy ring in the side chain. Such a PHA may be a homopolymer or may be a copolymer comprising two or more kinds of units.

To be more specific, the PHA may include those mentioned in *Int. J. Biol. Macromol.*, 1990, 12, 92-101, etc. for an alkyl group; in *Macromol. Chem.*, 1990, 191, 1957-1965, *Macromolecules*, 1991, 24, 5256-5260, *Macromolecules*, 1996, 29, 1762-1766, etc. for a phenyl ring; in *Macromolecules*, 1996, 29, 3432-3435, *Macromol. Chem. Phys.*, 1994, 195, 1665-1672, etc. for a phenoxy ring; in *Appl. Environ. Microbiol.* 1988, 54, 2924-2932, *Int. J. Biol. Macromol.*, 1990, 12, 85-91, *J. Polym. Sci. Part A*, 1995, 33, 1367-1374, *Macromolecules*, 1994, 27, 1675-1679, *Macromolecules*, 1998, 31, 1480-1486, etc. for a double bond; in *Macromolecules*, 1998, 31, 4760-4763, etc. for a triple bond; in *Macromolecules*, 1990, 23, 3705-3707, *J. Chem. Soc. Polym. Commun.*, 1990, 31, 404-406, *Macromolecules*, 1992, 25, 1852-1857, *Macromolecules*, 1996, 29, 4572-4581, etc. for a halogen element; and in *Macromolecules*, 1999, 32, 7389-7395, etc. for an epoxy ring; and carbon numbers of the PHA are various as well.

Specific examples of the macromolecular compound include poly(3-hydroxy alkanoate) and poly(4-hydroxy alkanoate) which have been well known to be produced mostly by living body and, particularly, by fermentation production of microbe. To be more specific, poly(3-hydroxy butyrate) may be particularly listed. Needless to say, the above-mentioned ones are mere examples and all macromolecular compounds containing a polymerization unit which is capable of forming a macromolecule by the process of the present invention are included. In addition, a combination of plural kinds of polymerization units may be included. There is no particular limitation on the degree of polymerization so far as the enzymatic reaction proceeds.

Although there is no particular limitation on the enzymatic polymerization reaction which can be used for the present invention, it is possible to list a reaction using, for example, hydroxy alkanoate coenzyme A as acyl coenzyme A and, in that case, PHA is produced as the macromolecular compound.

(2-2) CoA Enzyme

For the macromolecular polymerization enzyme used in the present invention, any enzyme may be used so far as it is a macromolecular polymerization enzyme which synthesizes a macromolecular compound using the substance produced by the thioester exchange reaction of the present invention as a substrate. For example, in case hydroxy alkanoate CoA is used as a substrate for the production of PHA, it is possible to use polyhydroxy alkanoate synthase (PHAS) which is an enzyme. With regard to a method for the preparation of a macromolecular polymerization enzyme, various methods such as a method of extracting and purifying of an enzyme from living organism cells and a method of extracting and purifying of an enzyme from an incubated product of living organism may be used, and an example is that PHAS is able to be extracted and purified from microbe cells. However, in the conventional extracting and purifying method, the amount of the enzyme to be obtained is limited to be very small and, therefore, in recent years, gene of PHAS is isolated utilizing a genetic recombination technique (*J. Biol. Chem.*, 1989, 264, 15298-15303; *J. Bacteriol.*, 1988, 170, 4431-4436; *J. Bacteriol.*, 1988, 170, 5837-5847) to highly express whereby the macromolecular polymerization enzyme is able to be separated and purified in a large amount (*J. Biochemistry*, 1994, 33, 9311-9320; *Protein Expression Purif.*, 1996, 7; 203-211) In addition to using as it is, the enzyme used in the macromolecular polymerization reaction of the present invention may also be used after being modified such as an immobilized enzyme.

Although there is no particular limitation on the source of living organisms wherefrom the macromolecular polymerization enzyme is derived, examples thereof are genus *Ralstonia*, genus *Pseudomonas*, genus *Chromatium*, genus *Ectothiorhodospira* and many microbes which have been well known for the production of PHA. It is also possible to obtain a macromolecular polymerization enzyme from a genetic recombinant having a macromolecular polymerization enzyme gene derived from those living organisms as a donor. An example is that gene of PHAS of *Ralstonia eutropha* ATCC 17699 is isolated, its recombinant *Escherichia coli* is prepared and incubated, and a desired PHAS is extracted and purified from the incubated product and is able to be used as a catalyst for a macromolecular polymerization reaction.

(2-3) Acyl Group Donor

The acyl group donor used in the macromolecular production reaction according to the present invention is the same as that in the above-mentioned highly efficient acyl group transfer reaction except that the acyl group is able to be a constituting unit for the macromolecular substance and acyl ester of aromatic thiol is preferred. Examples of the aromatic thiol are the same as those mentioned already.

Production process of thioester is mentioned, for example, in *J. Am. Chem. Soc.*, 1973, 22, 5829.

The thioester is able to be subjected to a thioester exchange reaction to easily convert to an acyl CoA which is thioester of CoA by co-existing with CoA salt under an alkaline condition (Int. Symp. Bacterial Polyhydroxyalkanoates, 1996, 28-35).

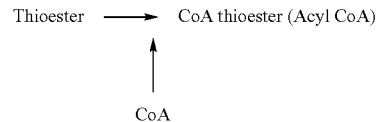

(2-4) Acyl Group Receptor

In an in vitro polymerization method, CoA thioester is used as a substrate for the enzyme and PHA is polymerized by the reaction of the enzyme and, at the same time, a liberated CoA is released into the reaction system. The CoA thioester contains both of that which was poured thereinto at the beginning of the reaction and that which was produced as the reaction proceeded and, anyway, the products are a polymer and CoA (cf. the following formula).

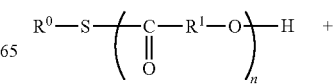

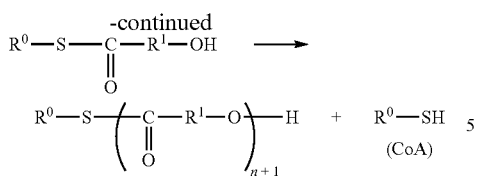

(In the formula, $R^0$ is an organic group wherein $R^0$—SH stands for CoA; $R^1$ is any alkylene; and n is an integer corresponding to degree of polymerization.)

In the present invention, the above two reactions, i.e. a thioester exchange reaction and a macromolecular polymerization reaction are combined and are carried out by making them to coexist in a reaction system to produce a macromolecular compound. Thus, CoA which is liberated into a reaction system after the polymerization reaction and has not been utilized again is made to react with thioester which is put into the reaction system whereby thioester of CoA is synthesized again and used as a substrate for the polymerization reaction once again (cf. the following formula).

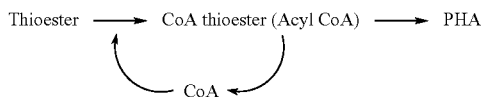

As a result, it is now possible to obtain a macromolecular compound as a product more than the equivalent amount of the CoA put into the reaction system. Particularly when the turnover of the reaction where the CoA is repeatedly thioesterified and liberated becomes higher, it is possible to significantly lower the industrial production cost of the macromolecular compound.

A higher CoA concentration in the reaction system becomes high as the polymerization proceeds may have an adverse effect on the enzymatic reaction, and the present invention is very effective in enhancing the productivity of PHA by suppressing the concentration. As such, the present invention is a process for producing PHA in high efficiency.

There is no particular limitation on the reaction condition of the present invention and that is similar to those in the highly efficient acyl group transfer reaction. As an example of the condition to promote the enzymatic reaction, the reaction temperature is 0° C. to 60° C., preferably 10° C. to 50° C., more preferably 20° C. to 40° C. Simply, it is also possible to conduct the reaction at room temperature. The desirable pH range to conduct the reaction is 3 to 12, preferably 5 to 10, more preferably 7 to 9.

As used herein, the state where the thioester exchange reaction and the macromolecular polymerization reaction coexist is a state where the thioester exchange reaction and the macromolecular polymerization reaction are present in the same aqueous solution, organic solvent or a mixed solution thereof or a state where they are present in the same reaction container in a solution or in plural solutions under a mixed state or a separated state. The separated state of the plural solutions in layers includes a state where a layer is present in oil drops or in a visibly suspended state. Anyway, it is sufficient if the state necessary for the thioester exchange reaction and the macromolecular polymerization reaction is maintained in a united manner. As a starting substance therefor, a thioester which is able to be efficiently produced industrially is to be made into thioester of CoA in the reaction system and used as a substrate for the polymerization reaction to produce a macromolecular compound.

BEST MODE FOR CARRYING OUT THE INVENTION

The present invention will now be illustrated in more detail hereinafter although the present invention is not limited by those Examples at all.

EXAMPLE 1

Synthesis of Acyl Thiophenol (Thiophenyl Palmitate)

Anhydrous dichloromethane (6 mL) was added to a well-dried and nitrogen-substituted flask and well stirred with cooling on ice. A 2M trimethyl aluminum (2 mL) was slowly added thereto. Further, thiophenol was slowly added thereto. After the mixture was stirred at room temperature for 1 hour and 30 minutes, ethyl palmitate dissolved in 6 mL of anhydrous dichloromethane was slowly added thereto to conduct a reaction. The reaction was monitored by TLC. After completion of the reaction, 20 mL of dichloromethane was added to the reaction solution and then a 3% aqueous solution of hydrochloric acid was added until no more generation of bubbles was observed. The solution was transferred to a separating funnel, washed with a 3% aqueous solution of hydrochloric acid for three times and with saturated saline for two times, dried over magnesium sulfate, filtered to remove magnesium sulfate and the filtrate was concentrated using an evaporator to give an oily solution in dark yellow color. This was separated and purified by a silica gel column chromatography (eluent:hexane/ethyl acetate=2/1) to give thiophenyl palmitate.

EXAMPLE 2

Preparation of Serine C-Palmitoyl Transferase (SPT)

A crude SPT enzyme extract was prepared from a transformant where the above-mentioned enzyme derived from genus *Sphingomonas* was cloned to *Escherichia coli*. Preparation of the Present Transformant and Method for purification of SPT were in accordance with the descriptions in *The Journal of Biological Chemistry*, 276, 18249-18256 (2001) by H. Ikushiro, et al.

Firstly, primers (SEQ ID NO: 1 and SEQ ID NO: 2) coding N-terminal sequence and C-terminal sequence were prepared from total base sequence of the above SPT and a DNA fragment corresponding to the SPT coding region was made by a PCR under the following condition using a chromosome DNA of *Sphingomonas paucimobilis* as a template. At that time, NcoI site for connecting to a vector and Hind III site were formed for the primer for N-terminal and for the primer for C-terminal, respectively.

```
[Primers]
Primer for N-terminal:
5'-accatgaccgaagccgccgctca-3'    (SEQ ID NO: 1)

Primer for C-terminal:
5'-taagctttcagccgatgacgccg-3'    (SEQ ID NO: 2)
```

[Composition of Reaction Solution]
  LA Taq polymerase
  Standard buffer attached to said enzyme
  Template chromosome <1 µg
  Primer: each 1 µM
  dNTP: each 200 µM
  Liquid volume: 25 µL to 100 µL
[Reaction Condition]
  Denaturation temperature: 94° C. for 30 seconds
  Annealing temperature: 40+0.25° C./cycle for 30 seconds
  Elongation temperature: 72° C. for 90 seconds The prepared PCR fragment was subjected to an agarose gel electrophoresis, extracted from the gel and recovered by means of a column. The fragment was treated with a restriction enzyme NcoI-HindIII and ligated with NcoI-HindIII fragment of a plasmid pET21d and a BL21 (DE3) strain of the host *Escherichia coli* was transformed thereby.

The resulting transformant was incubated on 5 mL of an LB medium containing 50 ppm of ampicillin at 35° C. for 16 hours and cells were recovered by centrifugation and washed with physiological saline. The washed cells were re-suspended in 2 mL of buffer for SPT (20 mM of phosphate buffer (pH 6.5, containing 0.1 mM of EDTA, 5 mM of DTT, 0.1 mM of AEBSF (protease inhibitor) and 0.02 mM of PLP)) and crushed for about 10 minutes using an ultrasonic crusher with ice-cooling and a non-crushed product was removed by centrifugation (12,000 rpm for 10 minutes) to give a crude enzyme extract.

EXAMPLE 3

Coupling of Ester Exchange Reaction with CoA Enzymatic Reaction (Uniform Aqueous System)

CoA sodium salt (2 mg) and 1 mg of L-serine were dissolved in 5 mL of 100 nM HEPES-NaOH buffer (containing 10 µM PLP, pH 8.0) and well stirred using a magnetic stirrer. That was mixed with a solution of 3.5 mg of thiophenyl palmitate in 0.1 mL of acetonitrile. While the stirring speed was made reduced to such an extent that a gentle mixing was resulted, 0.5 mL of crude SPT enzyme solution was added and the mixture was made to react at 37° C. for 24 hours. The solution was made alkaline with 1 mL of 2N ammonia solution and the product in the solution was extracted and recovered with 5 mL of chloroform/methanol (2:1 (v/v)). The extract liquid was filtered, appropriately concentrated and subjected to a quantitative determination for 3-ketodihydrosphingosine according to the following analytic method whereupon the produced amount was about 1.0 mg.

[Analysis of Sphingosines]

Quantitative analysis of sphingosines was carried out using a TLC-FID (Iatroscan) according to a method mentioned in *Journal of Chromatography*, 284, 433-440 (1984) by M. Tanaka, et al. That is, 1 µL of a solution where 1 to 10 mg of dihydrosphingosine (sphinganine) or 3-ketodihydrosphingosine as a standard sample was dissolved in 1 mL of methanol was subjected to a chromato-rod S II (silica gel) and developed by a primary developing solution (chloroform-methanol-15N ammonia solution=60:10:1). The rod after the development was subjected to an Iatroscan TH-10 TLC/FID Analyser (manufactured by Iatron) whereupon sphingosines were detected and quantified.

With regard to more detailed quantitative analysis of sphingoid bases, the product was made into a fluoroderivative and then separated and analyzed by a high-performance liquid chromatography by referring, for example, to a literature (*Analytical Biochemistry*, 298 (2001), 283-292).

The reaction solution (75 µL) to be described later was taken and 425 µL of 70.6 mM triethylamine/ethanol solution was added thereto and stirred therewith. The precipitate was removed by centrifuging for 5 minutes, 100 µL of the supernatant liquid was taken in an HPLC sample vial (300 µL small amount insert), 20 µL of an AQC reagent (manufactured by Waters) solution was added thereto and the mixture was stirred immediately. After being made to react at room temperature for 40 minutes or longer, the product was analyzed according to the following HPLC condition.

Main device: LC-VP series (Shimadzu Corporation) (pump: LC-10 ADVP; column oven: CTO-10ACVP; autosampler: SIL-10AF; system controller: SCL-10AVP)

Detector: Fluorescence detector 821-FP (Nippon Bunko), Ex. 244 nm, Em. 398 nm, Gain×100

Column: Shodex F-511A, 35° C.

Eluent: Acetonitrile/methanol/water/trimethylamine=480/320/190/7; 1.5 ml/min.

Method for regeneration of column: In the regeneration method of the literature, column pressure is apt to be too high, which is likely to cause error, so it was modified as follows.

Regenerating solution, acetonitrile/methanol = 60/40

↓

Switching from eluent to regenerated solution by a linear gradient for one minute (1.5 ml/min)

↓

Regenerated solution was passed for 12 minutes (1.5 ml/min)

↓

Switching from regenerated solution to eluent by a linear gradient for one minute (1.5 ml/min)

↓

After the eluent was passed for 2 minutes (1.5 ml/min), the condition was returned to the analytical condition Analytical cycle: A column regenerating system is placed for each sample analysis. Upon regeneration, no sample was infused.

COMPARATIVE EXAMPLE 1

CoA Enzymatic Reaction without Using a Coupling System

Palmitoyl CoA (10 mg) and 1 mg of L-serine were dissolved in 5 mL of 100 mM HEPES-NaOH buffer (containing 10 µM PLP; pH 8.0) and well stirred using a magnetic stirrer. While the stirring speed was reduced to such an extent that a mild mixing was resulted, 0.5 mL of a crude SPT enzyme solution was added and the mixture was made to react at 37° C. for 24 hours. The solution was made alkaline with 1 mL of 2N ammonia solution and the product in the solution was extracted and recovered with 5 mL of chloroform/methanol (2:1, (v/v)). The extract liquid was filtered, concentrated appropriately and analyzed by the same manner as in Example 3 whereupon the produced amount of 3-ketodihydrosphingosine was about 0.02 mg.

EXAMPLE 4

Coupling of the Ester Exchange Reaction with the CoA Enzymatic Reaction (Oil-Water Bilayer System)

CoA sodium salt (2 mg) and 1 mg of L-serine were dissolved in 5 mL of 100 mM HEPES-NaOH buffer (containing 10 μM PLP; pH 8.0) and well stirred using a magnetic stirrer. A solution prepared by dissolving 3.5 mg of thiophenyl palmitate in 5 mL of hexane was mixed therewith. While the stirring speed was reduced to such an extent that a mild mixing was resulted, 0.5 mL of a crude SPT enzyme solution was added and the mixture was made to react at 37° C. for 24 hours. The solution was made alkaline with 1 mL of 2N ammonia solution and the product in the solution was extracted and recovered with 5 mL of chloroform/methanol (2:1, (v/v)). The extract was filtered, concentrated appropriately and 3-ketodihydrosphingosine was quantified by the same manner as in Example 3 whereupon the produced amount was about 2.2 mg.

Hereinafter, examples of the process for macromolecularization according to the present invention will be listed.

REFERENTIAL EXAMPLE 1 (1)

Synthesis of 3-Oxobutyrate Ethyl Ester

On ice, 3.9 g of Meldrum's acid was dissolved in 18 ml of dehydrated dichloromethane in a dry flask and stirred and a solution of 4.3 g of pyridine and 2.2 g of acetyl chloride dissolved in 18 ml of dehydrated dichloromethane was slowly added thereto under a nitrogen stream. The mixture was stirred at 0° C. for one hour and then at room temperature for two hours. The mixed solution was transferred to a separating funnel, washed with 3% hydrochloric acid solution for two times and with saturated saline for two times, dried over magnesium sulfate and evaporated in vacuo to give 3.6 g of crude oily acylated Meldrum's acid in dark orange color which solidified slowly. The crude acyl Meldrum's acid was refluxed in 80 ml of dehydrated ethanol. At that time, generation of carbon dioxide was observed. The solvent was removed by evaporation to give 1.3 g of crude 3-oxobutyrate ethyl ester as a red oil. This was purified by a column chromatography (20 cm×1 cm diameter; eluent was hexane:ethyl acetate=2:1) using silica gel 60 to give 0.60 g of pure 3-oxobutyrate ethyl ester as a slightly yellow oil. The yield to the unpurified substance was 46%. Result of NMR analysis of this compound is as follows.

$^1$H NMR (in CDCl$_3$) δ4.20 (q, J=7.1 Hz, 2H), 3.47 (s, 2H), 2.27 (s, 3H), 1.28 (t, J=7.1 Hz, 3H);
$^{13}$C NMR (in CDCl$_3$) δ201.06, 167.44, 61.52, 50.29, 30.32, 14.29

REFERENTIAL EXAMPLE 1 (2)

Synthesis of 3-Hydroxybutyrate Ethyl Ester

A solution of 75.6 mg of sodium borohydride dissolved in 2 ml of dehydrated ethanol was stirred in a dry flask and a solution of 520 mg of 3-oxobutyrate ethyl ester in 2 ml of dehydrated ethanol was slowly added thereto. The mixture was stirred at room temperature for two hours and then 4 ml of water was added. The mixed solution was transferred to a separating funnel, extracted with dichloromethane for two times, dried over magnesium sulfate and evaporated in vacuo to give 282 mg of 3-hydroxybutyrate as a light yellow oil. Result of NMR analysis of this compound is as follows.

$^1$H NMR (in CDCl$_3$) δ 4.17 (q, J=7.1 Hz, 2H), 4.17 (m, 1H), 2.46 (m, 2H), 1.28 (t, J=7.1 Hz, 3H), 1.23 (d, J=6.3 Hz, 3H);
$^{13}$C NMR (in CDCl$_3$) δ 172.93, 64.28, 60.68, 42.91, 22.49, 14.18

REFERENTIAL EXAMPLE 1 (3)

Synthesis of 3-Hydroxybutyrate Thiophenyl Ester

In a dry flask on ice, 6 ml of dehydrated dichloromethane was stirred and 2 ml of 2M trimethyl aluminum was slowly added thereto under a nitrogen stream. After that, 2 mmol of thiophenol was slowly added thereto. The mixture was stirred at room temperature for 30 minutes and then 3-hydroxybutyrate dissolved in 6 ml of dehydrated dichloromethane was added thereto. The reaction was monitored by a TLC. To this mixed solution was added 20 ml of dichloromethane and, until generation of bubbles stopped, 20 ml of 3% hydrochloric acid solution was added. The mixed solution was transferred to a separating funnel, washed with 3% hydrochloric acid solution for two times and with saturated saline for two times, dried over magnesium sulfate and evaporated in vacuo to give 532 mg of crude oily 3-hydroxybutyrate thiophenyl ester in dark yellow color. This was purified by a column chromatography (20 cm×1 cm diameter; eluent was hexane:ethyl acetate=2:1) using silica gel 60 to give 125 mg of pure 3-hydroxybutyrate thiophenyl ester as a transparent oil. The yield to the unpurified substance was 24%. Result of NMR analysis of this compound is as follows.

$^1$H NMR (in CDCl$_3$) δ 7.38 (s, 5H), 4.33 (m, 1H), 2.83 (m, 2H), 1.25 (d, 3H);
$^{13}$C NMR (in CDCl$_3$) δ198.24, 134.90, 130.07, 129.69, 127.61, 65.23, 52.02, 22.85

REFERENTIAL EXAMPLE 1 (4)

Synthesis of 3-Hydroxybutyrate CoA Thioester

A solution of 9.8 mg of 3-hydroxybutyrate thiophenyl ester dissolved in 0.1 ml of acetonitrile was added to a solution of 39.5 mg of coenzyme A sodium salt dissolved with stirring in 0.5 ml of 100 mM calcium phosphate buffer (pH 8.0) in a small glass bottle. The mixture was stirred at room temperature for three hours and then 0.13 ml of 1M phosphoric acid was added thereto. The mixed solution was washed with 0.5 ml of diethyl ether for three times and evaporated in vacuo to give 30 mM of 3-hydroxybutyrate CoA thioester solution.

REFERENTIAL EXAMPLE 2 (1)

Synthesis of (R)-3-Hydroxybutyrate Thiophenyl Ester tert-Butyl dimethylsilyl chloride (2.53 g) was dissolved in anhydrous dimethylformamide and stirred, 3.4 g of imidazole was added thereto and the mixture was stirred for 15 minutes on ice in an nitrogen stream. Then 0.5 g of (R)-3-hydroxybutyrate dissolved in anhydrous dimethylformamide was further added thereto followed by stirring at room temperature for one night. To the reaction solution was added 60 ml of saturated saline and extraction with a solution of diethyl ether:petroleum ether=1:3 was repeated for five times. The extract liquid was dried over magnesium sulfate and evaporated in vacuo. This was dissolved in a solution of methanol:

tetrahydrofuran=2:1, 10 ml of an aqueous solution containing 1.5 g of potassium carbonate was added and the mixture was stirred at room temperature for one night. The reaction solution was diluted with saturated saline, adjusted to pH 3.0 with 1M sulfuric acid and extracted with a solution of diethyl ether:petroleum ether=1:3 for five times. The extract liquid was dried over magnesium sulfate, evaporated in vacuo and dried in vacuo to give 3-(tert-butyldimethylsilyl) butyrate. On ice, 870 mg of 3-(tert-butyldimethylsilyl) butyrate and 452 mg of thiophenol were dissolved in 6 ml of dichloromethane, a solution of 846 mg of dicyclohexyl carbodiimide dissolved in 2 ml of dichloromethane was added thereto followed by stirring and the mixture was stirred at room temperature for ten hours. Diethyl ether (20 ml) was added thereto, the mixture was filtered, the solvent was removed by evaporation and a flush chromatography was conducted (eluent was hexane containing 5% of ethyl acetate) to give 330 mg of 3-(tert-butyldimethylsilyl) butyrate thiophenyl ester. This was dissolved in 2 ml of acetonitrile and then an acetonitrile solution containing 6 ml of 5% hydrogen fluoride was further added thereto. After the reaction for 20 minutes, a saturated sodium hydrogen carbonate solution was added until no more bubble was generated, the mixture was extracted with diethyl ether and the extract was washed with saturated saline, dried over magnesium sulfate and evaporated in vacuo to give 81 mg of (R)-3-hydroxybutyrate thiophenyl ester.

REFERENTIAL EXAMPLE 2 (2)

Synthesis of (R)-3-Hydroxybutyrate CoA Thioester

A 3-hydroxybutyrate CoA thioester solution was prepared by the same manner as in the synthesis of 3-hydroxybutyrate CoA thioester.

REFERENTIAL EXAMPLE 3 (1)

Synthesis of 3-Oxovalerate Ethyl Ester

On ice, 3.9 g of Meldrum's acid was dissolved in 18 ml of dehydrated dichloromethane in a dry flask and stirred and a solution of 4.3 g of pyridine and 2.5 g of propionyl chloride dissolved in 18 ml of dehydrated dichloromethane was slowly added thereto under a nitrogen stream. The mixture was stirred at 0° C. for one hour and then at room temperature for two hours. The mixed solution was transferred to a separating funnel, washed with 3% hydrochloric acid solution for two times and with saturated saline for two times, dried over magnesium sulfate and evaporated in vacuo to give 3.4 g of crude oily acylated Meldrum's acid in dark orange color which solidified slowly. The crude acyl Meldrum's acid was refluxed in 80 ml of dehydrated ethanol. At that time, generation of carbon dioxide was observed. The solvent was removed by evaporation to give 1.7 g of crude 3-oxovalarate ethyl ester in red oil. This was purified by a column chromatography (20 cm×1 cm diameter; eluent was hexane:ethyl acetate=2:1) using silica gel 60 to give 0.50 g of pure 3-oxovalerate ethyl ester as a slightly yellow oil. The yield to the unpurified substance was 29%. Result of NMR analysis of this compound is as follows.
$^1$H NMR (in CDCl$_3$) δ 4.19 (q, J=7.1 Hz, 2H), 3.40 (s, 2H), 2.58 (q, J=7.2 Hz, 2H), 1.28 (t, J=7.2 Hz, 3H), 1.08 (t, J=7.2 Hz, 3H);
$^{13}$C NMR (in CDCl$_3$) δ203.48, 180.07, 61.33, 49.03, 36.32, 14.13, 7.56

REFERENTIAL EXAMPLE 3 (2)

Synthesis of 3-Hydroxyvalerate Ethyl Ester

A solution of 75.6 mg of sodium borohydride dissolved in 1 ml of dehydrated ethanol was stirred in a dry flask and a solution of 288 mg of 3-oxovalerate ethyl ester in 1 ml of dehydrated ethanol was slowly added thereto. The mixture was stirred at room temperature for two hours and then 2 ml of water was added. The mixed solution was transferred to a separating funnel, extracted with dichloromethane for two times, dried over magnesium sulfate and evaporated in vacuo to give 212 mg of 3-hydroxyvalerate as a light yellow oil. Result of NMR analysis of this compound is as follows.
$^1$H NMR (in CDCl$_3$) δ 4.17 (q, J=7.1 Hz, 2H), 3.94 (m, 1H), 2.45 (m, 2H), 1.57 (m, 2H), 1.27 (t, J=7.1 Hz, 3H), 0.96 (t, J=7.3 Hz, 3H);
$^{13}$C NMR (in CDCl$_3$) δ173.30, 69.64, 60.91, 41.46, 29.77, 14.40, 10.07

REFERENTIAL EXAMPLE 3 (3)

Synthesis of 3-Hydroxyvalerate Thiophenyl Ester

In a dry flask on ice, 3 ml of dehydrated dichloromethane was stirred and 1 ml of 2M trimethyl aluminum was slowly added thereto under a nitrogen stream. After that, 1 mmol of thiophenol was slowly added thereto. The mixture was stirred at room temperature for 30 minutes and then 3-hydroxyvalerate dissolved in 3 ml of dehydrated dichloromethane was added thereto. The reaction was monitored by a TLC. To this mixed solution was added 10 ml of dichloromethane and, until generation of bubbles stopped, 10 ml of 3% hydrochloric acid solution was added. The mixed solution was transferred to a separating funnel, washed with 3% hydrochloric acid solution for two times and with saturated saline for two times, dried over magnesium sulfate and evaporated in vacuo to give 258 mg of crude oily 3-hydroxyvalerate thiophenyl ester in dark yellow color. This was purified by a column chromatography (20 cm×1 cm diameter; eluent was hexane: ethyl acetate=2:1) using silica gel 60 to give 44 mg of pure 3-hydroxyvalerate thiophenyl ester as a transparent oil. The yield to the unpurified substance was 17%. Result of NMR analysis of this compound is as follows.
$^1$H NMR (in CDCl$_3$) δ 7.39 (s, 5H), 4.04 (m, 1H), 2.82 (m, 2H), 1.60 (m, 2H), 0.98 (t, J=7.1 Hz, 3H);
$^{13}$C NMR (in CDCl$_3$) δ198.30, 134.67, 129.83, 129.46, 127.31, 70.04, 50.03, 29.67, 9.96

REFERENTIAL EXAMPLE 3 (4)

Synthesis of 3-Hydroxyvalerate CoA Thioester

A solution of 42 mg of 3-hydroxyvalerate thiophenyl ester dissolved in 1 ml of acetonitrile was added to a solution of 79 mg of coenzyme A sodium salt dissolved with stirring in 2 ml of 100 mM calcium phosphate buffer (pH 8.0) in a small glass bottle. The mixture was stirred at room temperature for three hours and then 0.53 ml of 1M phosphoric acid was added thereto. The mixed solution was washed with 2 ml of diethyl ether for three times and evaporated in vacuo to give 33 mM of 3-hydroxyvalerate CoA thioester solution.

REFERENTIAL EXAMPLE 4

Preparation and Purification of Enzyme

A restriction enzyme EcoRI and SmaI fragment (about 5 kbp) were digested from a genomic DNA of *Ralstonia eutro-* pha ATCC 17699 and cloned to pUC18 to give a plasmid pTI 305 containing a PHA synthetic enzyme gene (PHAS). After that, three kinds—fragment of SmaI and BamHI of vector pQE 30 (manufactured by Qiagen) and BamHI.NotI fragment (140 bp) of DNA amplified by a PCR using the following two kinds of primers—were mixed and ligated using NotI.StuI fragment (1.6 kbp) of pTI 305 and pTI 305 as templates whereupon a plasmid PQEREC was prepared. This was introduced into Escherichia coli BL 21 (pREP4) to prepare Escherichia coli BL21 (pQEREC) for the preparation of enzyme. The Escherichia coli was incubated in 1,000 ml of LB medium at 30° C. for 16 hours so that enzyme was accumulated in cells and the cells were broken by an ultrasonic treatment whereupon a soluble protein in the cells was recovered. The protein was passed through an Ni-NTA agarose gel column so that (His)-PhaC (six histidine being added to N-terminal) was specifically adsorbed with the column. After washing the column, (His)-PhaC was eluted using imidazole and, after dialysis, 10 mg thereof was obtained as a pure enzyme. Molecular weight of the enzyme by an SDS-PAGE was 65 kDa.

Condition for the PCR

```
Sense primer:
aaggatccatggcgaccggcaaaggcgcgg      (SEQ ID NO: 3)

Antisense primer:
tgcagcggaccggtggcctcggcctgccc       (SEQ ID NO: 4)
```

Cycle: 30 cycles×(94° C. for 45 seconds, 58° C. for 30 seconds and 72° C. for 60 seconds)

EXAMPLE 5

Polymerization of Poly((R)-3-Hydroxybutyrate)

To 5 ml of 100 mM potassium phosphate solution was added 0.015 mg of the enzyme followed by well stirring at room temperature. While the stirring speed was reduced to such an extent that a gentle mixing was resulted and temperature of the solution was kept at 30° C., 5 ml of 1 mM CoA sodium solution and 0.5 ml of 20 mM 3-hydroxybutyrate thiophenyl ester solution (being dissolved in a 1:1 solution of 100 mM potassium phosphate solution and acetonitrile) were added thereto little by little and the mixture was further made to react at 30° C. for 24 hours. After that, the solution was washed with 20 ml of hexane for three times and then the product in the solution was extracted and recovered with 10 ml of chloroform. That was repeated for three times. The extract liquid was filtered, dropped into 300 ml of methanol and allowed to stand for 24 hours. The resulting precipitate was recovered by filtration and dried in a vacuum drier to give 0.4 mg of poly((R)-3-hydroxybutyrate). Its molecular weight (GPC calculated as polystyrene) was Mw=970,000. Result of NMR analysis of the compound is as follows.

$^1$H NMR (in CDCl$_3$) δ5.26 (m, H), 2.53 (m, 2H), 1.25 (s, 3H);
$^{13}$C NMR (in CDCl$_3$) δ169.53, 67.99, 41.16, 20.15

COMPARATIVE EXAMPLE 2

Polymerization of Poly((R)-3-Hydroxybutyrate)

An enzyme (0.015 mg) was added to 5 ml of 100 mM potassium phosphate solution and well stirred at room temperature. While the stirring speed was reduced to such an extent that a gentle mixing was resulted and temperature of the solution was kept at 30° C., 5 ml of 1 mM CoA sodium solution was added thereto little by little and the mixture was further made to react at 30° C. for 24 hours. After that, the solution was washed with 20 ml of hexane for three times and the product in the solution was extracted and recovered with 10 ml of chloroform. That was repeated for three times. The extract was filtered, dropped into 300 ml of methanol and allowed to stand for 24 hours. However, no precipitate was obtained.

EXAMPLE 6

Polymerization of ((R)-3-Hydroxybutyrate)

An enzyme (0.015 mg) was added to 5 ml of 100 mM potassium phosphate solution and well stirred at room temperature. While the stirring speed was reduced to such an extent that a gentle mixing was resulted and temperature of the solution was kept at 30° C., 5 ml of 1 mM 3-hydroxybutyrate CoA solution and 0.5 ml of 20 mM 3-hydroxybutyrate thiophenyl ester solution (being dissolved in a 1:1 solution of 100 mM potassium phosphate solution and acetonitrile) were added thereto little by little and the mixture was further made to react at 30° C. for 24 hours. After that, the solution was washed with 20 ml of hexane for three times and the product in the solution was extracted and recovered with 10 ml of chloroform. That was repeated for three times. The extract liquid was filtered, dropped into 300 ml of methanol and allowed to stand for 24 hours. The resulting precipitate was recovered by filtration and dried by a vacuum drier to give 0.3 mg of poly((R)-3-hydroxybutyrate).

COMPARATIVE EXAMPLE 3

Polymerization of Poly((R)-3-Hydroxybutyrate)

An enzyme (0.015 mg) was added to 5 ml of 100 mM potassium phosphate solution and well stirred at room temperature. While the stirring speed was reduced to such an extent that a gentle mixing was resulted and temperature of the solution was kept at 30° C., 5 ml of 1 mM 3-hydroxybutyrate CoA was added thereto little by little and the mixture was further made to react at 30° C. for 24 hours. After that, the solution was washed with 20 ml of hexane for three times and the product in the solution was extracted and recovered with 10 ml of chloroform. That was repeated for three times. The extract liquid was filtered, dropped into 300 ml of methanol and allowed to stand for 24 hours. The resulting precipitate was recovered by filtration and dried by a vacuum drier to give 0.2 mg of poly ((R)-3-hydroxybutyrate).

COMPARATIVE EXAMPLE 4

An enzyme (0.015 mg) was added to 5 ml of 100 mM potassium phosphate solution and well stirred at room temperature. While the stirring speed was reduced to such an extent that a gentle mixing was resulted and temperature of the solution was kept at 30° C., 0.5 ml of 20 mM 3-hydroxybutyrate thiophenyl ester solution (being dissolved in a 1:1 solution of 100 mM potassium phosphate solution and acetonitrile) were added thereto little by little and the mixture was further made to react at 30° C. for 24 hours. After that, the solution was washed with 20 ml of hexane for three times and the product in the solution was extracted and recovered with 10 ml of chloroform. That was repeated for three times. The extract liquid was filtered, dropped into 300 ml of methanol and allowed to stand for 24 hours. However, no precipitate was formed.

EXAMPLE 7

Polymerization of Poly(3-Hydroxyvalerate)

To 5 ml of 100 mM potassium phosphate solution was added 0.015 mg of the enzyme followed by well stirring at room temperature. While the stirring speed was reduced to such an extent that a gentle mixing was resulted, 5 ml of 1 mM (R,S)-3-hydroxyvalerate CoA and 0.5 ml of 20 mM 3-hydroxyvalerate thiophenyl ester solution (being dissolved in a 1:1 solution of 100 mM potassium phosphate solution and acetonitrile) were added thereto little by little and the mixture was further made to react at room temperature for 24 hours. After that, the solution was washed with 20 ml of hexane for three times and then the product in the solution was extracted and recovered with 10 ml of chloroform. That was repeated for three times. The extract liquid was filtered, dropped into 300 ml of methanol and allowed to stand for 24 hours. The resulting precipitate was recovered by filtration and dried in a vacuum drier to give 0.3 mg of poly((R)-3-hydroxyvalerate) Result of NMR analysis of the compound is as follows.

$^1$H NMR (in CDCl$_3$) δ 5.12 (m, H), 2.56 (m, 2H), 1.53 (m, 2H), 0.81 (t, 3H);

$^{13}$C NMR (in CDCl$_3$) δ169.71, 72.26, 39.17, 27.23, 9.76

COMPARATIVE EXAMPLE 5

Polymerization of Poly((3-Hydroxyvalerate)

An enzyme (0.015 mg) was added to 5 ml of 100 mM potassium phosphate solution and well stirred at room temperature. While the stirring speed was reduced to such an extent that a gentle mixing was resulted, 5 ml of 1 mM (R,S)-3-hydroxyvalerate CoA was added thereto little by little and the mixture was further made to react at room temperature for 24 hours. After that, the solution was washed with 20 ml of hexane for three times and the product in the solution was extracted and recovered with 10 ml of chloroform. That was repeated for three times. The extract liquid was filtered, dropped into 300 ml of methanol and allowed to stand for 24 hours. The resulting precipitate was recovered by filtration and dried by a vacuum drier to give 0.1 mg of poly((R)-3-hydroxyvalerate).

EXAMPLE 8

Polymerization of Poly((R)-3-Hydroxybutyrate) from (R)-3-Hydroxybutyrate Thiophenyl Ester An enzyme (0.015 mg) was added to 5 ml of 100 mM sodium phosphate solution (pH 7.5) and 1 mM CoA sodium solution and stirred keeping the temperature of the solution at 30° C. A hexane solution (5 ml) of 10 mM (R)-3-hydroxybutyrate thiophenyl ester was layered thereon. The stirring speed was reduced to such an extent that a gentle mixing was resulted and reaction was conducted at 30° C. for 24 hours. After the reaction, the hexane layer was removed and the product in the solution was extracted with 5 ml of chloroform from the aqueous layer. That was repeated for two times. The extract liquid was filtered, dropped into 200 ml of methanol and allowed to stand at 4° C. for 24 hours. The resulting precipitate was recovered by filtration and dried by a vacuum drier to give 1.5 mg of poly((R)-3-hydroxybutyrate). Molecular weight (GPC calculated as polystyrene) was Mw=1,070,000. Reaction turnover of thio-esterification and liberation of the added CoA was 3.4 times.

COMPARATIVE EXAMPLE 6

Polymerization of Poly((R)-3-Hydroxybutyrate) from (R)-3-Hydroxybutyrate CoA Thioester An enzyme (0.015 mg) was added to 5 ml of 100 mM sodium phosphate solution (pH 7.5) and 1 mM (R)-3-hydroxybutyrate CoA thioester solution and stirred keeping the temperature of the solution at 30° C. The stirring speed was reduced to such an extent that a gentle mixing was achieved and reaction was conducted at 30° C. for 24 hours. After the reaction, the hexane layer was removed and the product in the solution was extracted with 5 ml chloroform from the aqueous layer. That was repeated for two times. The extract liquid was filtered, dropped into 200 ml of methanol and allowed to stand at 4° C. for 24 hours. The resulting precipitate was recovered by filtration and dried by a vacuum drier to give 0.4 mg of poly ((R)-3-hydroxybutyrate).

COMPARATIVE EXAMPLE 7

Polymerization of Poly((R)-3-Hydroxybutyrate) from (R)-3-Hydroxybutyrate Thiophenyl Ester An enzyme (0.015 mg) was added to 5 ml of 100 mM sodium phosphate solution (pH 7.5) and stirred keeping the temperature of the solution at 30° C. A hexane solution (5 ml) of 10 mM (R)-3-hydroxybutyrate thiophenyl ester was layered thereon. The stirring speed was reduced to such an extent that a gentle mixing was resulted and reaction was conducted at 30° C. for 24 hours. After the reaction, the hexane layer was removed and the product in the solution was extracted with 5 ml of chloroform from the aqueous layer. That was repeated for two times. The extract liquid was filtered, dropped into 200 ml of methanol and allowed to stand at 4° C. for 24 hours. No precipitate was observed.

INDUSTRIAL APPLICABILITY

In accordance with the process of the present invention using an acyltransferase, it is now possible to continuously carry out the reaction and to improve its productivity significantly without supplementary addition of very expensive acyl coenzyme A (acyl CoA). Accordingly, various kinds of compounds are able to be produced by a novel coupling method, which enables utilization of acyltransferase to an industrial production method. According to the present invention, in a production process of sphingoid bases, a thioester exchange reaction is combined with an enzymatic reaction whereby sphingoid bases which have been difficult to produce in the conventional fermentation process are able to be accumulated and produced without the problem of cytotoxicity, reproduction reaction of acyl CoA which is a coenzyme essential for the reaction is also able to be carried out in the same reaction solution system and consumed amount of the coenzyme drastically reduces whereby sphingoid bases are able to be economically produced. According to the present invention, various sphingoid bases are now able to be produced at a low cost in a pure form and the use becomes significantly broad.

Moreover, when a thioester exchange reaction is combined with an in vitro polymerization in a production process of PHA, the starting substance for the reaction is able to be substituted with an easily synthesizable thiophenyl ester, reproduction reaction of acyl CoA which is a coenzyme essential for the reaction is also able to be carried out in the same reaction solution system and consumed amount of the coenzyme drastically reduces whereby various PHAs are able to be economically and efficiently produced on an industrial scale and the use becomes significantly broad.

---

The invention claimed is:

1. In a production process of a macromolecular compound using an acyltransferase reaction, in which an acyl group of acyl coenzyme A (acyl CoA) is transferred, wherein the reaction is carried out by production and/Pr reproduction of acyl coenzyme A from coenzyme A in a reaction system by a chemical thioester exchange reaction with an acyl group donor which is an acyl ester of a thiol compound;

wherein an acyl group donor, acyl group receptor, coenzyme A and acyltransferase are contained in the reaction system at the same time, an acyl group of the acyl group donor is transferred to coenzyme A by a chemical thioester exchange reaction to give an acyl coenzyme A and an acyl group of the acyl coenzyme A is transferred to the acyl group receptor;

wherein the acyltransferase is a macromolecular polymerization enzyme and a macromolecular compound is synthesized in a reaction in which an acyl group donor, acyl group receptor, coenzyme A and acyltransferase are contained in the reaction system at the same time, an acyl group of the acyl group donor is transferred to coenzyme A by a chemical thioester exchange reaction to give an acyl coenzyme A and an acyl group of the acyl coenzyme A is transferred to the acyl group receptor; and a production process of polyester in which the macromolecular compound is polyester.

2. The production process of the polyester according to claim 1, wherein the polyester is polyhydroxy alkanoate.

3. The production process of the polyester according to claim 2, wherein the polyhydroxy alkanoate is poly(3-hydroxy alkanoate).

4. The production process of the polyester according to claim 3, wherein the poly(3-hydroxy alkanoate) is poly(3-hydroxy butyrate).

5. The production process of the polyester according to claim 1, wherein an acyltransferase reaction is repeated using acyl coenzyme A or a product by the acyltransferase reaction as an acyl group receptor whereby the macromolecular compound is produced.

6. The production process of the polyester according to claim 1, wherein the acyl thioester is acyl ester of aromatic thiol.

7. The production process of the polyester according to claim 6, wherein the acyl ester of aromatic thiol is hydroxyalkanoate thiophenyl ester.

8. The production process of the polyester according to claim 7, wherein the hydroxyalkanoate thiophenyl ester is 3-hydroxyalkanoate thiophenyl ester.

9. The production process of the polyester according to claim 8, wherein the 3-hydroxyalkanoate thiophenyl ester is 3-hydroxybutyrate thiophenyl ester.

10. The production process of the polyester according to claim 1, wherein the macromolecular polymerization enzyme is polyhydroxy alkanoate synthase.

11. The production process of the polyester according to claim 10, wherein the polyhydroxy alkanoate synthase is derived from genus *Ralstonia*.

12. The production process of the polyester according to claim 11, wherein the genus *Ralstonia* is *Ralstonia eutropha*.

13. The production process of the polyester according to claim 12, wherein *Ralstonia eutropha* is *Ralstonia eutropha* ATCC 17699.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Sphingomonas paucimobilis

<400> SEQUENCE: 1
accatgaccg aagccgccgc tca                                            23

<210> SEQ ID NO 2
<211> LENGTH: 23
<212> TYPE: DNA
<213> ORGANISM: Sphingomonas paucimobilis

<400> SEQUENCE: 2
taagctttca gccgatgacg ccg                                            23

<210> SEQ ID NO 3
<211> LENGTH: 30
<212> TYPE: DNA
<213> ORGANISM: Artificial Sequence
<220> FEATURE:
<223> OTHER INFORMATION: chemically synthesized PCR primer

<400> SEQUENCE: 3
aaggatccat ggcgaccggc aaaggcgcgg                                     30

<210> SEQ ID NO 4
<211> LENGTH: 29
<212> TYPE: DNA
<213> ORGANISM: Artificial Sequence
<220> FEATURE:
<223> OTHER INFORMATION: chemically synthesized PCR primer

<400> SEQUENCE: 4
tgcagcggac cggtggcctc ggcctgccc                                      29